(12) United States Patent
Johnson et al.

(10) Patent No.: US 7,361,946 B2
(45) Date of Patent: Apr. 22, 2008

(54) SEMICONDUCTOR DEVICE-BASED SENSORS (75) Inventors: Jerry W. Johnson, Raleigh, NC (US); Edwin L. Piner, Cary, NC (US); Kevin J. Linthicum, Cary, NC (US)

(73) Assignee: Nitronex Corporation, Durham, NC (US)

( * ) Notice: Subject to any disclaimer, the term of this patent is extended or adjusted under 35 U.S.C. 154(b) by 0 days.

(21) Appl. No.: 10/879,704

(22) Filed: Jun. 28, 2004

(65) Prior Publication Data

US 2005/0285155 A1 Dec. 29, 2005

(51) Int. Cl.
*H01L 23/58* (2006.01)

(52) U.S. Cl. .................. 257/253; 257/414; 435/180

(58) Field of Classification Search ............ 257/253, 257/258, 414; 435/180
See application file for complete search history.

(56) References Cited

U.S. PATENT DOCUMENTS

| | | | |
|---|---|---|---|
| 4,020,830 A | 5/1977 | Johnson et al. | |
| 4,180,771 A | 12/1979 | Guckel | |
| 4,411,741 A | 10/1983 | Janata | |
| 4,636,827 A | 1/1987 | Rudolf | |
| 4,791,465 A | 12/1988 | Sakai et al. | |
| 4,843,440 A | 6/1989 | Huang | |
| 4,877,582 A | 10/1989 | Oda et al. | |
| 4,961,833 A | 10/1990 | Sakai et al. | |
| 5,078,855 A | 1/1992 | Mochizuki et al. | |
| 5,143,696 A | 9/1992 | Haas et al. | |
| 5,192,987 A | 3/1993 | Khan et al. | |
| 5,239,188 A | 8/1993 | Takeuchi et al. | |
| 5,279,795 A | 1/1994 | Hughes et al. | |
| 5,290,393 A | 3/1994 | Nakamura | |
| 5,296,395 A | 3/1994 | Khan et al. | |
| 5,309,085 A | 5/1994 | Sohn | |
| 5,389,571 A | 2/1995 | Takeuchi et al. | |
| 5,393,993 A | 2/1995 | Edmond et al. | |
| 5,466,348 A | 11/1995 | Holm-Kennedy | |
| 5,523,589 A | 6/1996 | Edmond et al. | |
| 5,576,563 A | 11/1996 | Chung | |

(Continued)

FOREIGN PATENT DOCUMENTS

DE 3430941 3/1985

(Continued)

OTHER PUBLICATIONS

Ando, Y. et al., "10-W/mm AlGan-GaN HFET With a Field Modulating Plate," IEEE Electron Device Lett. 24(5):289 (2003).

(Continued)

*Primary Examiner*—Evan Pert
*Assistant Examiner*—Tan Tran
(74) *Attorney, Agent, or Firm*—Wolf, Greenfield & Sacks, P.C.

(57) ABSTRACT

Semiconductor device-based chemical sensors and methods associated with the same are provided. The sensors include regions that can interact with chemical species being detected. The chemical species may, for example, be a component of a fluid (e.g., gas or liquid). The interaction between the chemical species and a region of the sensor causes a change in a measurable property (e.g., an electrical property) of the device. These changes may be related to the concentration of the chemical species in the medium being characterized.

15 Claims, 5 Drawing Sheets

U.S. PATENT DOCUMENTS

| | | | |
|---|---|---|---|
| 5,633,192 A | 5/1997 | Moustakas et al. | |
| 5,679,965 A | 10/1997 | Schetzina | |
| 5,693,545 A | 12/1997 | Chung et al. | |
| 5,739,554 A | 4/1998 | Edmond et al. | |
| 5,741,724 A | 4/1998 | Ramandi et al. | |
| 5,760,426 A | 6/1998 | Marx et al. | |
| 5,786,606 A | 7/1998 | Nishio et al. | |
| 5,815,520 A | 9/1998 | Furushima | |
| 5,838,029 A | 11/1998 | Shakuda | |
| 5,838,706 A | 11/1998 | Edmond et al. | |
| 5,874,747 A | 2/1999 | Redwing et al. | |
| 5,915,164 A * | 6/1999 | Taskar et al. | 438/47 |
| 5,929,467 A | 7/1999 | Kawai et al. | |
| 6,041,643 A | 3/2000 | Stokes et al. | |
| 6,051,849 A | 4/2000 | Davis et al. | |
| 6,064,078 A | 5/2000 | Northrup et al. | |
| 6,064,082 A | 5/2000 | Kawai et al. | |
| 6,069,021 A | 5/2000 | Terashima et al. | |
| 6,100,545 A | 8/2000 | Chiyo et al. | |
| 6,111,280 A * | 8/2000 | Gardner et al. | 257/253 |
| 6,120,600 A | 9/2000 | Edmond et al. | |
| 6,121,121 A | 9/2000 | Koide | |
| 6,139,628 A | 10/2000 | Yuri et al. | |
| 6,146,457 A | 11/2000 | Solomon | |
| 6,153,010 A | 11/2000 | Kiyoku et al. | |
| 6,156,581 A | 12/2000 | Vaudo et al. | |
| 6,177,688 B1 | 1/2001 | Linthicum et al. | |
| 6,180,270 B1 | 1/2001 | Cole et al. | |
| 6,201,262 B1 | 3/2001 | Edmond et al. | |
| 6,255,198 B1 | 7/2001 | Linthicum et al. | |
| 6,261,929 B1 | 7/2001 | Gehrke et al. | |
| 6,261,931 B1 | 7/2001 | Keller et al. | |
| 6,265,289 B1 | 7/2001 | Zheleva et al. | |
| 6,291,319 B1 | 9/2001 | Yu et al. | |
| 6,329,063 B2 | 12/2001 | Lo et al. | |
| 6,380,108 B1 | 4/2002 | Linthicum et al. | |
| 6,391,748 B1 | 5/2002 | Temkin et al. | |
| 6,403,451 B1 | 6/2002 | Linthicum et al. | |
| 6,420,197 B1 | 7/2002 | Ishida et al. | |
| 6,426,512 B1 | 7/2002 | Ito et al. | |
| 6,440,823 B1 | 8/2002 | Vaudo et al. | |
| 6,441,393 B2 | 8/2002 | Goetz et al. | |
| 6,459,712 B2 | 10/2002 | Tanaka et al. | |
| 6,465,814 B2 | 10/2002 | Kasahara et al. | |
| 6,486,502 B1 | 11/2002 | Sheppard et al. | |
| 6,498,111 B1 | 12/2002 | Kapolnek et al. | |
| 6,521,514 B1 | 2/2003 | Gehrke et al. | |
| 6,524,932 B1 | 2/2003 | Zhang et al. | |
| 6,548,333 B2 | 4/2003 | Smith | |
| 6,576,972 B1 | 6/2003 | Parsons | |
| 6,583,034 B2 | 6/2003 | Ramdani et al. | |
| 6,583,454 B2 | 6/2003 | Sheppard et al. | |
| 6,586,781 B2 | 7/2003 | Wu et al. | |
| 6,610,144 B2 | 8/2003 | Mishra et al. | |
| 6,611,002 B2 | 8/2003 | Weeks et al. | |
| 6,617,060 B2 | 9/2003 | Weeks et al. | |
| 6,624,452 B2 | 9/2003 | Yu et al. | |
| 6,649,287 B2 | 11/2003 | Weeks, Jr. et al. | |
| 6,765,240 B2 | 7/2004 | Tischler et al. | |
| 6,765,241 B2 | 7/2004 | Ohno et al. | |
| 6,777,278 B2 | 8/2004 | Smith | |
| 6,841,409 B2 | 1/2005 | Onishi | |
| 6,849,882 B2 | 2/2005 | Chavarkar et al. | |
| 2001/0042503 A1 | 11/2001 | Lo et al. | |
| 2002/0020341 A1 | 2/2002 | Marchand et al. | |
| 2002/0117681 A1 | 8/2002 | Weeks et al. | |
| 2002/0117695 A1 | 8/2002 | Borges | |
| 2003/0080294 A1* | 5/2003 | Matocha et al. | 250/339.15 |
| 2003/0136333 A1 | 7/2003 | Semond et al. | |
| 2004/0130002 A1* | 7/2004 | Weeks et al. | 257/622 |
| 2004/0178468 A1 | 9/2004 | McFarland et al. | |
| 2005/0051804 A1* | 3/2005 | Yoshida | 257/213 |
| 2005/0053524 A1* | 3/2005 | Keersmaecker et al. | 422/88 |
| 2005/0097941 A1 | 5/2005 | Sandvik et al. | |
| 2005/0110053 A1* | 5/2005 | Shur et al. | 257/253 |

FOREIGN PATENT DOCUMENTS

| | | |
|---|---|---|
| EP | 0751392 | 1/1997 |
| EP | 1353170 | 10/2003 |
| JP | 61011652 | 1/1986 |
| JP | 62132160 | 6/1987 |
| WO | WO 96/41906 | 12/1996 |
| WO | WO 01/13436 A1 | 2/2001 |

OTHER PUBLICATIONS

Ando, Y. et al., "A 110-W AlGaN/GaN Heterojunction FET On Thinned Sapphire Substrate," Photonic and Wireless Devices Research Labs, NEC Corp. (2001).

Binari, S.C. et al., "Microwave Performance of GaN MESFETs," Electronics Lett. 30(15):1248 (1994).

Bindra, A., "Exotic Materials Squeeze More Juice Out of RF Power Amplifiers," www.elecdesign.com. ED Online ID # 2367, Jun. 24, 2002.

Borges, R. et al., "GaN HFETs on Silicon Target Wireless Infrastructure Market," Compound Semiconductor, p. 2 (Aug. 2003).

Brown, J.D. et al., "AlGaN/GaN HFETs Fabricated on 100-mm GaN on Silicon (111) Substrates," Solid-State Electronics 46:1535 (2002).

Brown, J.D. et al., "Performance of AlGaN/GaN HFETs Fabricated on 100mm Silicon Substrates for Wireless Basestation Applications," Nitronex Corporation, IEEE MTT-S Digest p. 833 (2004).

Chen, P. et al., "Growth of High Quality GaN Layers With AlN Buffer on Si(111) Substrates," J. Crystal Growth 225:150 (2001).

Chumbes, E. et al., "AlGaN/GaN High Electron Mobility Transistors on Si(111) Substrates," IEEE Trans. Electron Dev. 48(3):420 (2001).

Dadgar, A. et al., "Bright, Crack-Free InGaN/GaN Light Emitters on Si(111)," Phys. Stat. Sol. 192(2):308 (2002).

Dadgar, A. et al., "Metalorganic Chemical Vapor Phase Epitaxy of Crack-Free GaN on Si (111) Exceeding 1 μm in Thickness," Jpn. J. Appl. Phys. 39:L1183 (2000).

Dadgar, A. et al., "MOVPE Growth of GaN on Si(111) Substrates," J. Crystal Growth 248:556 (2003).

Elhamri, S. et al., "An Electrical Characterization of a Two Dimensional Electron Gas in GaN/AlGaN on Silicon Substrates," J. Appl. Phys. 95(12):7982 (2004).

Fanning, D. et al., "Dielectrically Defined Optical T-Gate for High Power GaAs pHEMTs," GaAsMANTECH Conference (2002).

Guha, S. et al., "Ultraviolet and Violet GaN Light Emitting Diodes on Silicon," Appl. Phys. Lett. 72(4):415 (1998).

Hageman, P.R. et al., "High Quality GaN Layers on Si(111) Substrates: AlN Buffer Layer Optimisation and Insertion of a SiN Intermediate Layer," Phys. Stat. Sol. 188(2):523 (2001).

Hanington, G. et al., "P/He Ion Implant Isolation Technology for AlGaN/GaN HFETs," Electronics Lett. 34(2):193 (1998).

Hanson, A. W. et al., "Development of a GaN Transistor Process for Linear Power Applications," Nitronex Corporation, Paper presented at the 2004 International Conference on Compound Semiconductor Manufacturing Technology (GaAs MANTECH), Miami, FL.

Hirosawa, K. et al., "Growth of Single Crystal $Al_2Ga_{1-\alpha}N$ Films on Si Substrates by Metalorganic Vapor Phase Epitaxy," Jpn. J. Appl. Phys. 32:L1039 (1993).

Ishikawa, H. et al., "High-Quality GaN on Si Substrate Using AlGaN/AlN Intermediate Layer," Phys. Stat. Sol. 176:599 (1999).

Johnson, J.W. et al., "12 W/mm AlGaN-GaN HFETs on Silicon Substrates," IEEE Electron Device Lett. 25(7):459 (2004).

Johnson, J.W. et al., "$Gd_2O_3$/GaN Metal-Oxide-Semiconductor Field-Effect Transistor," Appl. Phys. Lett. 77(20):3230 (2000).

Johnson, J.W. et al., "Material, Process, and Device Development of GaN-Based HFETs on Silicon Substrates," Nitronex Corporation, Electrochemical Society Proceedings Jun. 2004, 405 (2004).

Joshin, K. et al., "A 174 W High-Efficiency GaN HEMT Power Amplifier for W-CDMA Base Station Applications," Fujitsu Laboratories Ltd. (2003).

Kang, B.S. et al., "Gateless AlGaN/GaN HEMT Response to Block Co-Polymers," Solid-State Electronics 48:851 (2004).

Kang, B.S. et al., "Pressure-Induced Changes in the Conductivity of AlGaN/GaN High-Electron Mobility-Transistor Membranes," Appl. Phys. Lett. 85(14):2962 (2004).

Kikkawa, T. et al., "An Over 200-W Output Power GaN HEMT Push-Pull Amplifier with High Reliability," IEEE MTT-S Digest (2004).

Kim, J. et al., "Comparison of Pt/GaN and Pt/4H-SiC Gas Sensors," Solid-State Electronics 47:1487 (2003).

Kim, J. et al., "Hydrogen-Sensitive GaN Schottky Diodes," Solid-State Electronics 47:1069 (2003).

Kim, J. et al., "Reversible Barrier Height Changes in Hydrogen-Sensitive Pd/GaN Diodes," Appl. Phys. Lett. 82(5):739 (2003).

Lahreche, H. et al., "Optimisation of AlN and GaN Growth by Metalorganic Vapour-Phase Epitaxy (MOVPE) on Si(111)," J. Crystal Growth 217:13 (2000).

Lee, D. et al., "GaN Thin Films as Gas Sensors," Sensors and Actuators B 89:305 (2003).

Lee, I. et al., "Growth and Optical Properties of GaN on Si(111) Substrates," J. Crystal Growth 235:73 (2002).

Lei, T. et al., "Epitaxial Growth of Zinc Blende and Wurtzitic Gallium Nitride Thin Films on (001) Silicon," Appl. Phys. Lett. 59(8):944 (1991).

Liu, R. et al., "Atomic Arrangement at the AlN/Si (111) Interface," Appl. Phys. Lett. 83(5):860 (2003).

Lu, C. et al., "A New Pd-Oxide-$Al_{0.3}Ga_{0.7}As$ MOS Hydrogen Sensor," IEEE Electron Device Lett. 24(6):390 (2003).

Luther, B.P. et al., "High Temperature Pt Schottky Diode Gas Sensors on n-Type GaN," Sensors and Actuators B 56:164 (1999).

Mehandru, R. et al., "AlGaN/GaN HEMT Based Liquid Sensors," Solid-State Electronics 48:351 (2004).

Moser, N.A. et al., "Effects of Surface Treatments on Isolation Currents in AlGaN/GaN High-Electron-Mobility Transistors," Appl. Phys. Lett. 83(20):4178 (2003).

Nagy, W. et al., "Linearity Characteristics of Microwave Power GaN HEMTs," IEEE Transactions on Microwave Theory & Techniques 51(2):1 (2003).

Nakada, Y. et al., "GaN Heteroepitaxial Growth on Silicon Nitride Buffer Layers Formed on Si (111) Surfaces by Plasma-Assisted Molecular Beam Epitaxy," Appl. Phys. Lett. 73(6):827 (1998).

Newey, J., "GaN: Ready for Cellular 3G?," Compound Semiconductor, p. 21 (Jan./Feb. 2004).

Nikishin, S.A. et al., "High Quality GaN Grown on Si(111) by Gas Source Molecular Beam Epitaxy with Ammonia," Appl. Phys. Lett. 75(14):2073 (1999).

Nuttinck, S. et al., "Direct On-Wafer Non-Invasive Thermal Monitoring of AlGaN/GaN Power HFETs Under Microwave Large Signal Conditions," Paper Presented at European Microwave Week, Amsterdam, NL (2004).

Ohtani, A. et al., "Microstructure and Photoluminescence of GaN Grown on Si(111) by Plasma-Assisted Molecular Beam Epitaxy," Appl. Phys. Lett. 65(1):61 (1994).

Okamoto, Y. et al., "An 80W AlGaN/GaN Heterojunction FET With a Field-Modulating Plate," IEEE MTT-S Digest p. 225 (2003).

Osinsky, A. et al., "Visible-Blind GaN Schottky Barrier Detectors Grown on Si(111)," Appl. Phys. Lett. 72(5):551 (1998).

Palmour. J.W. et al., "Wide Bandgap Semiconductor Devices and MMICs for RF Power Applications," IEEE (2001).

Patel, S., "The Bottleneck on the Road to 3G," WirelessFuture Magazine (Jan./Feb. 2003).

Piner, E., "GaN Transistors and Power Amplifiers Close in on Commercialization," Compound Semiconductor (Jul. 2004).

Pyke, S., "Gallium Nitride Integrated Gas/Temperature Sensors for Fuel Cell System Monitoring for Hydrogen and Carbon Monoxide," Proceedings of the 2001 DOE Hydrogen Program Review NREL/CP-570-30535.

Rajagopal, P. et al., "Large-Area, Device Quality GaN on Si Using a Novel Transition Layer Scheme," Nitronex Corporation, Material Research Society Symposium Proceedings 743(3) (2003).

Rajagopal, P. et al., "MOCVD AlGaN/GaN HFETs on Si: Challenges and Issues," Symposium Y: GAN and Related Alloys, Nitronex Corporation, Material Research Society Symposium Proceedings, 798, 61-66 (2004).

Reitmeier, Z. et al., "Growth and Characterization of AlN and GaN Thin Films Deposited on Si(111) Substrates Containing a Very Thin Al Layer," Dept. Materials Science and Engineering, NC State University.

Schalwig, J. et al., "Gas Sensitive GaN/AlGaN-Heterostructures," Sensors and Actuators B 87:425 (2002).

Schalwig, J. et al., "Group III-Nitride-Based Sensors for Combustion Monitoring," Materials Sci. & Eng. B93:207 (2002).

Schalwig, J. et al., "Hydrogen Response Mechanism of Pt-GaN Schottky Diodes," Appl. Phys. Lett. 80(7):1222 (2002).

Semond, F. et al., "GaN Grown on Si(111) Substrate: From Two-Dimensional Growth to Quantum Well Assessment," Appl. Phys. Lett. 75(1):82 (1999).

Seon, M. et al., "Selective Growth of High Quality GaN on Si(111) Substrates," Appl. Phys. Lett. 76(14):1842 (2000).

Singhal, S. et al., "Gallium Nitride on Silicon HEMTs for Wireless Infrastructure Applications, Thermal Design and Performance," Nitronex Corporation, Paper presented at the European Microwave Week, Milan, Italy (2002).

Starikov, D. et al., "Radio-Frequency Molecular-Beam-Epitaxy Growth of III Nitrides for Microsensor Applications," J. Vac. Sci. Technol. B 19(4):1404 (2001).

Stutzmann, M. et al., "GaN-Based Heterostructures for Sensor Applications," Diamond and Related Materials 11:886 (2002).

Tanaka, S. et al., "Defeat Structure in Selective Area Growth GaN Pyramid on (111)Si Substrate," Appl. Phys. Lett. 76(19):2701 (2000).

Thompson, R. et al., "Improved Fabrication Process for Obtaining High Power Density AlGaN/GaN HEMTs," IEEE GaAs Digest p. 298 (2003).

Vescan, A. et5 al., "AlGaN/GaN HFETs on 100 mm Silicon Substrates for Commercial Wireless Applications," Phys. Stat. Sol. (c) 0(1):52 (2002).

Yagi, S. et al., "UV Dose Measurements of Photosensitive Dermatosis Patients by Polycrystalline GaN-Based Portable Self-Data-Acquisition UV Monitor," 76(6):669 (2002).

Zhao, G. et al., "A Novel Pt-AlGaN/GaN Heterostructure Schottky Diode Gas Sensor on Si," IEICE Trans, Fundamentals/ Commun./ Electron./Inf. & Syst. E85-A/B/C/D(1):1 (2002).

Zhao, Z.M. et al., "Metal-Semiconductor-Metal GaN Ultraviolet Photodetectors on Si(111)," Appl. Phys. Lett. 77(3):444 (2000).

Scharnagl, K., et al., "Enhanced room temperature gas sensing with metal oxides by means of the electroadsorptive effect in hybrid suspended gate FET" Sensors and Actuators B 57 (1999) 35-38.

International Search Report data Feb. 11, 2005, PCT/US2005/022490.

* cited by examiner

SEMICONDUCTOR DEVICE-BASED SENSORS

BACKGROUND OF INVENTION

The invention relates generally to semiconductor device-based sensors and, more particularly, to gallium nitride material-based transistors that function as chemical sensors and methods associated with the same.

Sensors may be used in many applications, for example, to detect the concentration of a chemical species. The chemical species may be a component of a fluid (e.g., a gas or a liquid) to which the sensor is exposed.

Semiconductor devices have been used as chemical sensors. For example, field effect transistor-based sensors may detect the concentration of a chemical species by measuring changes in drain current (i.e., source-to-drain current) that result from adsorption of the chemical species on the surface of the gate electrode. This adsorption may lead to a change in drain current. The change in the drain current may be related to the concentration of the adsorbed chemical species which, in turn, may be related to the concentration of the chemical species in the medium (e.g., fluid) being characterized.

SUMMARY OF INVENTION

The invention provides semiconductor device-based sensors, as well as methods associated with the same.

In one embodiment, a FET-based chemical sensor designed to detect a chemical species is provided. The sensor comprises a semiconductor material region. The sensor further comprises a source electrode, a drain electrode and a gate electrode, each formed on the semiconductor material region. The sensor further comprises a sensing region, separated from the gate electrode, and capable of interacting with the chemical species to change a measurable property of the chemical sensor.

In another embodiment, a FET-based chemical sensor designed to detect a chemical species is provided. The sensor comprises a silicon substrate; a transition layer formed on the silicon substrate; and, a gallium nitride material region formed on the transition layer. The sensor further comprises a source electrode, a drain electrode and a gate electrode, each formed on the gallium nitride material region. The sensor further comprises a sensing region, separate from the gate electrode, and capable of interacting with the chemical species to change a drain current of the chemical sensor.

In another embodiment, a semiconductor device-based chemical sensor is provided. The sensor comprises a semiconductor material region; and, a sensing electrode formed on the semiconductor material region. The sensing electrode is separated from electrodes needed for conventional operation of the device and is capable of interacting with the chemical species to change a measurable property of the chemical sensor.

In another embodiment, a semiconductor device-based chemical sensor is provided. The sensor comprises a semiconductor material region. A first electrode and a second electrode are formed on the semiconductor material region. A first electrical contact extends from a backside of the sensor to the first electrode; and a second electrical contact extends from a backside of the sensor to the second electrode. The sensor further comprises a sensing region, separated from the first electrode and the second electrode, and capable of interacting with the chemical species to change a measurable property of the chemical sensor.

In another embodiment, a method of detecting chemical species is provided. The method comprises exposing a FET-based chemical sensor to a medium comprising chemical species; and measuring changes in drain current of the sensor resulting from adsorption of the chemical species on a sensing region separated from the gate electrode to detect chemical species.

Other aspects, embodiments and features of the invention will become apparent from the following detailed description of the invention when considered in conjunction with the accompanying drawings. The accompanying figures are schematic and are not intended to be drawn to scale. In the figures, identical, or substantially similar components that are illustrated in various figures may be represented by a single numeral or notation. For purposes of clarity, not every component is labeled in every figure. Nor is every component of each embodiment of the invention shown where illustration is not necessary to allow those of ordinary skill in the art to understand the invention. All patent applications and patents incorporated herein by reference are incorporated by reference in their entirety. In case of conflict with incorporated references, the present specification, including definitions, will control.

DETAILED DESCRIPTION

The invention provides semiconductor device-based chemical sensors and methods associated with the same. The sensors include a sensing region that can interact with chemical species being detected. The chemical species may, for example, be a component of a fluid (e.g., gas or liquid). The interaction between the chemical species and a region of the sensor causes a change in a measurable property (e.g., an electrical property such as drain current) of the device. These changes may be related to the concentration of the chemical species in the medium being characterized. As described further below, the sensing region may be the combination of a sensing layer (e.g., a sensing electrode) and an underlying semiconductor material region, or an exposed semiconductor material (e.g., gallium nitride material) region. Sensors of the invention may be used in a wide variety of applications including engine emission monitoring, carbon dioxide detection and flue gas monitoring, amongst others.

Figure 1A:
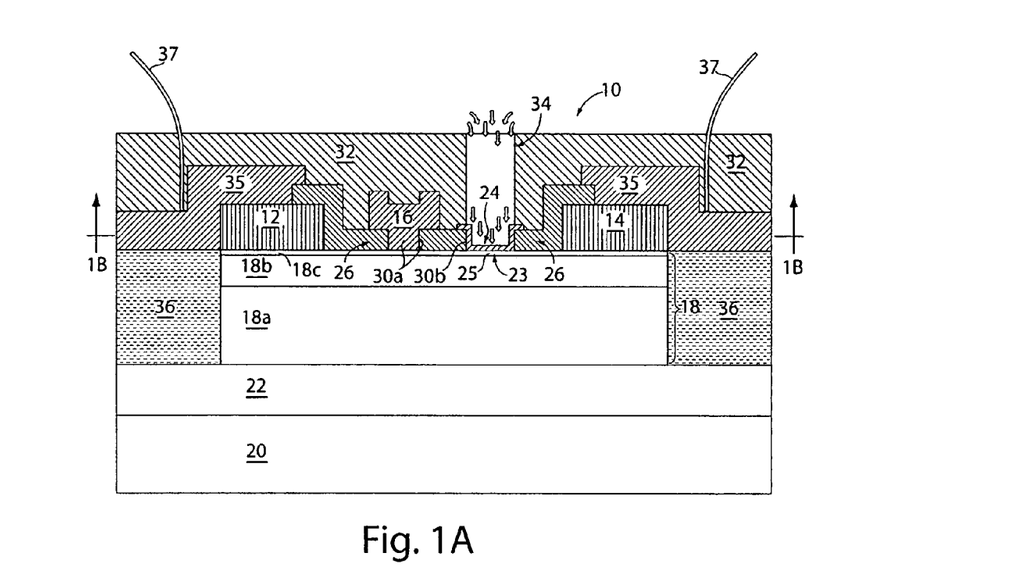
FIG. 1A is a cross-section of a field effect transistor (FET)-based chemical sensor including a sensing electrode according to an embodiment of the invention.
Figure 1B:
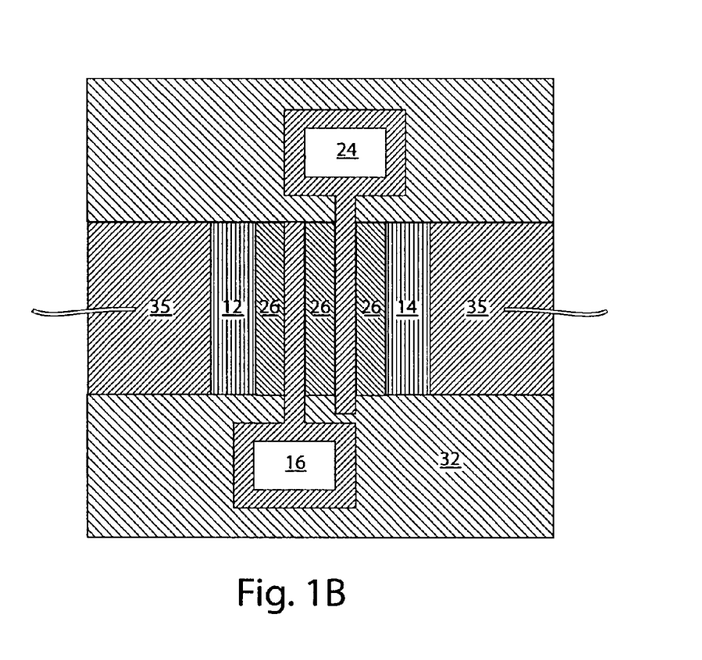
FIG. 1B is a top view of the sensor of FIG. 1A taken along line 1B-1B in FIG. 1A.

FIGS. 1A and 1B illustrate a semiconductor device-based sensor 10 according to one embodiment of the invention. In the illustrative embodiment, the sensor is a field effect transistor (FET) that includes a source electrode 12, a drain electrode 14 and a gate electrode 16 formed on a semiconductor material (e.g., gallium nitride material) region 18. The semiconductor material region is formed on a substrate 20 and, as shown, a transition layer 22 may be formed between the substrate and the semiconductor material region. The sensor includes a sensing region 23 between the source and the drain electrodes. In the illustrative embodiment, the sensing region comprises a sensing layer 24 and an underlying surface region 25 of the semiconductor material region. As shown, the sensing layer is a sensing electrode which, along with the gate electrode is defined, at least in part, by an electrode-defining layer 26.

During use, sensing region 23 is exposed to a medium (e.g., a fluid) that includes chemical species to be detected. As described further below, the chemical species in the medium (e.g., by following the direction of the schematic arrows in FIG. 1A) are adsorbed by the sensing layer which leads to an interaction between the species and the sensing layer. It is believed that this interaction results in a change in the surface potential of underlying surface region 25. This change in surface potential results in a change in a property (e.g., drain current) of the device which may be measured and related to the concentration of the species in the medium.

In some cases, it is believed that the chemical species may also diffuse through the sensing layer and directly interact with the underlying semiconductor material region 18. However, it should be understood that the invention is not limited to a particular mechanism by which the measurable property (e.g., drain current) of the device is changed and/or by which the surface potential of the underlying surface region changes. In embodiments of the invention, the chemical species interacts with a sensing region in some manner which results in the property change.

Though sensor 10 is an FET in the illustrative embodiment of FIGS. 1A and 1B, it should be understood that the invention encompasses other types of semiconductor device-based sensors as described further below.

When a layer is referred to as being "on" or "over" another layer or substrate, it can be directly on the layer or substrate, or an intervening layer may also be present. A layer that is "directly on" another layer or substrate means that no intervening layer is present. It should also be understood that when a layer is referred to as "on" or "over" another layer or substrate, it may cover the entire layer or substrate, or a portion of the layer or substrate.

Sensing layer 24 may be formed of any suitable material that is capable of interacting with a chemical species being detected in a manner that results in a change in a measurable property (e.g., drain current) of the sensor. In some cases, the sensing layer is formed of a conductive material (e.g., when the sensing layer is a sensing electrode). Suitable conductive sensing layer materials include, but are not limited to, metals, metal compounds and doped semiconductor materials. In some embodiments, the sensing layer comprises a noble metal (or one of its alloys) or a transition metal (or one of its alloys). For example, the sensing layer may comprise one or more of the following metals: platinum, palladium, iridium, ruthenium, nickel, copper, rhodium, molybdenum, iron, cobalt, titanium, vanadium, tantalum, tungsten, chromium, magnesium, gold, silver, aluminum, tin, osmium, magnesium, zinc, as well as alloys of these metals and compounds of these metals.

It should also be understood that the above-described conductive materials may be suitable when the sensing layer is not functioning as an electrode.

In other cases (e.g., when the sensing layer is not functioning as an electrode), the sensing layer may be formed of non-conductive materials such as dielectric materials or polymeric materials.

In some embodiments, the sensing layer may comprise more than one layer, each having a different composition. In some embodiments, one or more layer may be formed above the sensing layer, or between the sensing layer and the semiconductor material region.

The sensing layer material may be selected for its sensitivity to a particular chemical species. In cases when a highly sensitive sensor for a specific chemical species is desired, the sensing layer may preferably comprise a material that interacts with the chemical species in a manner that causes a relatively large change in surface potential of the underlying surface region. Suitable chemical species/material combinations are known in the art. For example, platinum or palladium electrodes are particularly well suited in hydrogen sensors; and, tin oxide is particularly well suited in $CO_2$ or CO detectors.

As shown in FIGS. 1A and 1B, the sensing layer may be a sensing electrode that is connected to a voltage source. When the sensing layer 24 is an electrode, it should be formed of a material that is sufficiently conductive. However, it should be understood that, in other embodiments, the sensing layer is not an electrode.

The sensing layer may have any suitable dimensions that enable the device to function as desired. Because the sensing layer is separated from the gate electrode, the dimensions and design of the sensing layer (e.g., when functioning as a sensing electrode) are not subject to any gate electrode design requirements. This increases the ability to tailor the dimensions of the sensing layer (e.g., when functioning as a sensing electrode) to improve sensor performance. In certain conventional sensors in which the gate electrode also functions as a sensing electrode (i.e., sensors that measure changes in drain current that result from adsorption of the chemical species on the surface of the gate electrode) there may be less freedom over the dimensions of this electrode because it must satisfy gate electrode requirements. Thus, because of the added dimensional freedom, sensors of the invention may have sensing layers that can be tailored to have improved sensor performance (i.e., sensitivity, responsivity, and recovery) compared to such conventional sensors.

For example, sensing layer 24 may be thinner than typically possible in conventional sensors in which the gate electrode also functions as a sensing electrode. Thin sensing electrodes permit relatively rapid diffusion of chemical species through the electrode to surface region 25 which can improve sensitivity and responsivity of the sensor. Also, thin sensing layers enable rapid out diffusion of chemical species which may lead to improved sensor recovery times. For example, the sensing layer may have a thickness of less than about 500 nanometers such as between about 5 nanometers and about 200 nanometers, or between about 50 nanometers and about 200 nanometers. In other embodiments, the sensing layers may be thicker and have a thickness of greater than about 500 nanometers.

The surface area of the sensing layer is designed to enable sufficient amounts of the chemical species to be adsorbed during operation. It may be advantageous in highly sensitive sensor applications for sensing layers to have a relatively large surface area when compared to the total channel surface area (i.e., the area defined between the source electrode and the drain electrode) of the device. In some cases, the ratio of the sensing electrode surface area to the total channel surface area is greater than about 0.35. In some cases, the ratio of the sensing electrode surface area to the total channel surface area is between about 0.20 and about 0.95; and, in some cases, between about 0.35 and about 0.60.

As noted above, in the embodiments of FIGS. 1A and 1B, sensing layer 24 is separated from gate electrode 16 so that the sensor includes four different electrodes when the sensing layer is a sensing electrode. Thus, an external voltage may be applied independently to each of the electrodes (i.e., source, gate, drain and sensing). Though, it should also be understood that the same external voltage may be applied to more than one of the different electrodes.

The ability to independently control the voltages applied to different electrodes (and, in particular, independently controlling the voltage applied to the sensing electrode and the gate electrode) may enhance the sensitivity and/or concentration range of the sensor for detecting a chemical species. In particular, the sensitivity and/or range may be enhanced as compared to conventional sensors that include a gate electrode that also functions as a sensing electrode because of the additional degree of freedom provided when the sensing electrode is separate from the gate electrode. In the embodiment of FIGS. 1A and 1B, the voltages applied to the different electrodes may be selected such that the dependency of the drain current on the concentration of adsorbed species is increased or maximized. In one preferred mode of operation, the gate electrode is biased near the maximum transconductance of the FET device while the source is grounded and the drain is positively biased. In this mode, small changes in the surface potential of the surface region 25 may translate into relatively large changes in drain current which results in high sensitivity.

In the illustrative embodiment, sensing region 23 is separated from the gate electrode which means that the sensing region is located at a different position on the device than the gate electrode and the region directly beneath the gate electrode. Thus, the sensing region is laterally separated from the gate electrode in the illustrative embodiment. As shown, the sensing region is positioned between the source and the drain electrodes and, more particularly, between the gate and drain electrodes. It should be understood that the sensing region may be positioned in other locations including between the source and gate electrodes.

In certain preferred embodiments, substrate 20 is a silicon substrate. As used herein, a silicon substrate refers to any substrate that includes a silicon surface. Examples of suitable silicon substrates include substrates that are composed entirely of silicon (e.g., bulk silicon wafers), silicon-on-insulator (SOI) substrates, silicon-on-sapphire substrate (SOS), and SIMOX substrates, amongst others. Suitable silicon substrates also include substrates that have a silicon wafer bonded to another material such as diamond, AlN, or other polycrystalline materials. Silicon substrates having different crystallographic orientations may be used. In some cases, silicon (111) substrates are preferred. In other cases, silicon (100) substrates are preferred.

It should be understood that other types of substrates may also be used including sapphire, silicon carbide, indium phosphide, silicon germanium, gallium arsenide, gallium nitride material, aluminum nitride, or other III-V compound substrates. However, in embodiments that do not use silicon substrates, all of the advantages associated with silicon substrates may not be achieved.

It should also be understood that though the illustrative embodiments include a substrate, other embodiments of the invention may not have a substrate. In these embodiments, the substrate may be removed during processing. In other embodiments, the substrate may also function as the semiconductor material region. That is, the substrate and semiconductor material region are the same region. For example, in these embodiments, the substrate (and semiconductor material region) may be formed of a gallium nitride material.

Substrate 20 may have any suitable dimensions. Suitable wafer diameters include, but are not limited to, 2 inches (50 mm), 4 inches (100 mm), 6 inches (150 mm), and 8 inches (200 mm). The diameter of the wafer depends, in part, on the type of substrate and the composition of the semiconductor material region. In some cases, it may be preferable for the substrate to be relatively thick, such as greater than about 125 micron (e.g., between about 125 micron and about 800 micron, or between about 400 micron and 800 micron). Relatively thick substrates may be easy to obtain, process, and can resist bending which can occur, in some cases, in thinner substrates. In other embodiments, thinner substrates (e.g., less than 125 microns) are used, though these embodiments may not have the advantages associated with thicker substrates, but can have other advantages including facilitating processing and/or reducing the number of processing steps. In some processes, the substrate initially is relatively thick (e.g., between about 200 microns and 800 microns) and then is thinned during a later processing step (e.g., to less than 150 microns).

In some preferred embodiments, the substrate is substantially planar in the final device or structure. Substantially planar substrates may be distinguished from substrates that are textured and/or have trenches formed therein (e.g., as in U.S. Pat. No. 6,265,289). In the illustrative embodiments, the regions/layers formed on the substrate (e.g., transition layer, gallium nitride material region, and the like) are also substantially planar. As described further below, such regions/layers may be grown in vertical (e.g., non-lateral) growth processes. Planar substrates and regions/layers can be advantageous in some embodiments, for example, to simplify processing. Though it should be understood that, in some embodiments of the invention, lateral growth processes may be used as described further below.

Transition layer 22 may optionally be formed on substrate 20 prior to the deposition of semiconductor material (e.g., gallium nitride material) region 18. The presence of the transition layer depends, in part, on the type of substrate and the composition of the semiconductor material region. When the substrate is a silicon substrate and the semiconductor material region is a gallium nitride material region, the presence of the transition layer may be preferred.

The transition layer may accomplish one or more of the following: reducing crack formation in the semiconductor material (e.g., gallium nitride material) region by lowering thermal stresses arising from differences between the thermal expansion rates of the semiconductor material region and the substrate; reducing defect formation in semiconductor material region by lowering lattice stresses arising from differences between the lattice constants of the semiconductor material region and the substrate; and, increasing conduction between the substrate and semiconductor material region by reducing differences between the band gaps of substrate and gallium nitride materials. The presence of the transition layer may be particularly preferred when utilizing silicon substrates and gallium nitride material regions because of the large differences in thermal expansion rates and lattice constants between gallium nitride materials and silicon. It should be understood that the transition layer also may be formed between substrate 20 and gallium nitride material region for a variety of other reasons. In some cases, for example when a silicon substrate is not used, the device may not include a transition layer.

The composition of transition layer 22 depends, at least in part, on the compositions of the substrate and of the semiconductor material region. In some embodiments which include a silicon substrate and a gallium nitride material region, the transition layer may preferably comprise a compositionally-graded transition layer having a composition that is varied across at least a portion of the layer. Suitable compositionally-graded transition layers, for example, have been described in commonly-owned U.S. Pat. No. 6,649,287, entitled "Gallium Nitride Materials and Methods," filed on Dec. 14, 2000, which is incorporated herein by reference. Compositionally-graded transition layers are particularly effective in reducing crack formation in the gallium nitride material region by lowering thermal stresses that result from differences in thermal expansion rates between the gallium nitride material and the substrate (e.g., silicon).

According to one set of embodiments, the transition layer is compositionally graded and formed of an alloy of gallium nitride such as $Al_xIn_yGa_{(1-x-y)}N$, $Al_xGa_{(1-x)}N$, and $In_yGa_{(1-y)}N$. In these embodiments, the concentration of at least one of the elements (e.g., Ga, Al, In) of the alloy is varied across at least a portion of the thickness of the transition layer. When the transition layer has an $Al_xIn_yGa_{(1-x-y)}N$ composition, x and/or y may be varied. When the transition layer has a $Al_xGa_{(1-x)}N$ composition, x may be varied. When the transition layer has a $In_yGa_{(1-y)}N$ composition, y may be varied.

In certain preferred embodiments, it is desirable for the transition layer to have a low gallium concentration at a back surface which is graded to a high gallium concentration at a front surface. It has been found that such transition layers are particularly effective in relieving internal stresses within the gallium nitride material region. For example, the transition layer may have a composition of $Al_xGa_{(1-x)}N$, where x is decreased from the back surface to the front surface of the transition layer (e.g., x is decreased from a value of 1 at the back surface of the transition layer to a value of 0 at the front surface of the transition layer). The composition of the transition layer, for example, may be graded discontinuously (e.g., step-wise) or continuously. One discontinuous grade may include steps of AlN, $Al_{0.6}Ga_{0.4}N$ and $Al_{0.3}Ga_{0.7}N$ proceeding in a direction toward the semiconductor material (e.g., gallium nitride material) region.

In some cases, the transition layer has a monocrystalline (i.e., single crystal) structure. In some embodiments, transition layer 22 has a constant (i.e., non-varying) composition across its thickness.

In some embodiments, sensors of the invention may also optionally include other layers that are not depicted in the figures. For example, the sensor may include one or more intermediate layers (e.g., a strain-absorbing layer). One or more intermediate layers may be formed, for example, between the substrate and the transition layer (e.g., a compositionally-graded transition layer) and/or between the transition layer and the semiconductor material region. These layers may have a constant composition.

Suitable intermediate layers, for example, have been described in U.S. Pat. No. 6,649,287, which is incorporated by reference above. In some embodiments, an intermediate layer may be formed of a nitride-based compound such as gallium nitride alloy (such as $Al_xIn_yGa_{(1-x-y)}N$, $Al_xGa_{(1-x)}N$, or $In_yGa_{(1-y)}N$), aluminum nitride, or aluminum nitride alloys.

Suitable strain-absorbing layers (e.g., silicon nitride material-based layers), for example, have been described in commonly-owned, co-pending U.S. patent application Ser. No. 10/879,703, entitled "Gallium Nitride Materials and Methods Associated With the Same", filed Jun. 28, 2004, which is incorporated herein by reference.

In some cases, the intermediate layer(s) have a monocrystalline structure. In other cases, the intermediate layer(s) may have an amorphous structure (e.g., when the intermediate layer is a strain-absorbing layer comprising a silicon nitride-based material).

As noted above, in some embodiments of the invention, it is preferable for semiconductor material region 18 to comprise a gallium nitride material, at least in the area of surface region 25. Gallium nitride materials have electrical properties (e.g., high piezoresistivity) that make them well suited for use in certain sensors of the present invention. For example, the surface potential of a gallium nitride material region may be strongly dependent on the adsorption of chemical species by the sensing region. This strong dependency can enable the sensor to be highly sensitive.

Gallium nitride materials are also generally able to withstand extreme conditions (such as high temperatures and/or corrosive environments) which certain other semiconductor materials cannot withstand. Thus, sensors that include gallium nitride material semiconductor regions may be able to operate under certain extreme conditions (and, thus, in certain applications) that sensors that include semiconductor regions formed of materials other than gallium nitride material.

As used herein, the phrase "gallium nitride material" refers to gallium nitride (GaN) and any of its alloys, such as aluminum gallium nitride ($Al_xGa_{(1-x)}N$), indium gallium nitride ($In_yGa_{(1-y)}N$), aluminum indium gallium nitride ($Al_xIn_yGa_{(1-x-y)}N$), gallium arsenide phosporide nitride ($GaAs_aP_bN_{(1-a-b)}$), aluminum indium gallium arsenide phosporide nitride ($Al_xIn_yGa_{(1-x-y)}As_aP_bN_{(1-a-b)}$), amongst others. Typically, when present, arsenic and/or phosphorous are at low concentrations (i.e., less than 5 weight percent). In certain preferred embodiments, the gallium nitride material has a high concentrations of gallium and nitrogen. In high gallium concentration embodiments, the sum of (x+y) may be less than 0.4, less than 0.2, less than 0.1, or even less. In some cases, it is preferable for the gallium nitride material layer to have a composition of GaN (i.e., x+y=0) or $Al_xGa_{(1-x)}N$ (y=0). In some cases, when the gallium nitride material layer has a composition of $Al_xGa_{(1-x)}N$, x is less than about 0.4. Gallium nitride materials may be doped n-type or p-type, or may be intrinsic. Suitable gallium nitride materials have been described in U.S. Pat. No. 6,649,287, incorporated by reference above.

As shown in certain embodiments, semiconductor material region may include multiple semiconductor layers (e.g., 18a, 18b, 18c) Layer 18b may have a different composition than layer 18a. For example, layer 18b may be formed of a first gallium nitride material and layer 18a may be formed of a second gallium nitride material. In certain embodiments, it may be preferable for the gallium nitride material of layer 18b to have an aluminum concentration that is greater than the aluminum concentration of the gallium nitride material of layer 18a. For example, the value of x in the gallium nitride material of layer 18b (with reference to any of the gallium nitride materials described above) may have a value that is between 0.05 and 1.0 greater than the value of x in the gallium nitride material of layer 18a, or between 0.05 and 0.5 greater than the value of x in the gallium nitride material of layer 18a. For example, layer 18b may be formed of $Al_{0.26}Ga_{0.74}N$, while layer 18a is formed of GaN. This difference in aluminum concentration may lead to formation of a highly conductive region at the interface of the layers 18b, 18a (i.e., a 2-D electron gas region) which can increase the sensitivity of the surface potential of surface region 25 which, in turn, can increase the sensitivity of the sensor. In the illustrative embodiment, layer 18c may be formed of GaN.

In some embodiments, semiconductor material region 18 may be formed of only a single semiconductor material. Or, region 18 may be formed of a semiconductor material layer and other non-semiconductor layers including oxide layers and/or metallic layers. However, in these embodiments, it may be preferable for surface region 25 to comprise gallium nitride material to achieve the advantages associated with gallium nitride material described above.

It should also be understood that, in certain embodiments of the invention, semiconductor material region 18 may be formed primarily, or entirely, of semiconductor materials other than gallium nitride material. For example, the semiconductor material region may be formed of silicon, gallium arsenide, or other III-V compounds. However, at least some of the advantages associated with gallium nitride materials may not be achieved when using other semiconductor materials.

Semiconductor material region 18 is of high enough quality to permit operation of the sensor device. Preferably, the semiconductor material (e.g., gallium nitride material) region has a low crack level and a low defect level. As described above, transition layer 22 (particularly when compositionally-graded) may reduce crack and/or defect formation. In some embodiments, the semiconductor material region has a defect density of less than about $10^9$ defects/$cm^2$.

Gallium nitride materials having low crack levels have been described in U.S. Pat. No. 6,649,287 incorporated by reference above. In some cases, the semiconductor region may comprise gallium nitride materials having a crack level of less than 0.005 micron/$micron^2$ or a crack level of less than 0.001 micron/$micron^2$. In certain cases, it may be preferable for the semiconductor region to comprise gallium nitride material that is substantially crack-free as defined by a crack level of less than 0.0001 micron/$micron^2$.

In certain cases, the semiconductor material region includes a layer or layers which have a monocrystalline (i.e., single crystal) structure. In cases when the semiconductor region comprises gallium nitride material, the gallium nitride material may have a single crystal structure such as a Wurtzite (hexagonal) structure.

The thickness of semiconductor material region 18 and the number of different layers are dictated, at least in part, by the requirements of the specific device. At a minimum, the thickness of the semiconductor material region is sufficient to permit formation of the desired structure or device (e.g., FET). The semiconductor region may have a thickness of greater than 0.1 micron, though not always. In other cases, the semiconductor material region has a thickness of greater than 0.5 micron, greater than 2.0 microns, or even greater than 5.0 microns.

As noted above, in the illustrative embodiment, electrode-defining layer 26 defines, at least in part, gate electrode 16 and sensing layer 24 (which is a sensing electrode). A first via 30a is formed in the electrode-defining layer in which the gate electrode is, in part, formed. The shape and the dimensions of the first via and, thus the gate electrode, can be controlled to improve certain electrical properties of the device. A second via 30b is formed in the electrode-defining layer in which the sensing layer is, in part, formed. The shape and the dimensions of the second via and, thus the sensing layer, can be controlled as desired.

Suitable compositions for the electrode-defining layer include, but are not limited to, nitride-based compounds (e.g., silicon nitride compounds), oxide-based compounds (e.g., silicon oxide compounds), polyimides, other dielectric materials, or combinations of these compositions (e.g., silicon oxide and silicon nitride). In some cases, it may be preferable for the electrode-defining layer to be a silicon nitride compound (e.g., $Si_3N_4$) or non-stoichiometric silicon nitride compounds.

In the illustrative embodiment, the electrode-defining layer is directly on semiconductor material region 18 and functions as a passivating layer that protects and passivates the surface of the semiconductor material region (e.g., gallium nitride material) region.

Suitable electrode-defining layers and gate electrode structures have been described in commonly owned, co-pending U.S. patent application Ser. No. 10/740,376, filed on Dec. 17, 2003, and entitled "Gallium Nitride Material Devices Including an Electrode-Defining Layer and Methods of Forming the Same", which is incorporated herein by reference.

It should be understood that, in certain embodiments, the sensors of the invention may not include a layer that defines the gate electrode and/or the sensing layer. In these cases, the gate electrode and/or sensing layer are otherwise patterned to form the desired structure.

The gate, source and drain electrodes may be formed of any suitable conducting material such as metals (e.g., gold, nickel), metal compounds (e.g., WSi, WSiN), alloys, semiconductors, or combinations of these materials. For example, the gate electrode may be formed of gold, nickel or both. Source and drain electrodes may be formed of gold, nickel, titanium, aluminum, platinum or silicon. Such compositions are known to those of ordinary skill in the art.

In some embodiments, the electrodes may extend into the semiconductor material region. For example, electrode material (e.g., metal) deposited on the surface of the gallium nitride material region may diffuse into the semiconductor material region during a subsequent annealing step (e.g., RTA) when forming the electrode. In particular, the source and drain electrodes may include such a portion diffused into the semiconductor material region. As used herein, such electrodes are still considered to be formed on the semiconductor material region.

The sensor shown in FIGS. 1A and 1B includes an encapsulation layer 32 which, as known to those of skill in the art, encapsulates underlying layers of the structure to provide chemical and/or electrical protection. The encapsulation layer may be formed of any suitable material including oxides or nitrides.

An opening 34 is formed in the encapsulation layer to allow chemical species access to the sensing electrode. In some embodiments, the opening may has sloped sidewalls so that the cross-sectional area of the opening decreases in a direction toward the sensing electrode which may enhance access to the sensing electrode.

In the illustrative embodiment, interconnects 35 are provided as conductive pathways that are connected to electrodes of the sensor. Though the illustrated interconnects are connected to the source and drain electrodes, it should also be understood that other conductive interconnects (not shown) may be connected to the other electrodes (e.g., gate and sensing). Bond wires 37 are generally provided to electrically connect the interconnects to a voltage source, thus, providing a conductive pathway from the voltage source to the electrodes on the device.

In the illustrative embodiment, amorphized regions 36 electrically isolate devices from adjacent devices (not shown). The amorphized regions may be formed by implanting a species (e.g., nitrogen ions) as described in commonly-owned, co-pending U.S. patent application Ser. No. 10/879, 695, entitled "Gallium Nitride Material Structures Including Isolation Regions and Methods", filed Jun. 28, 2004. It should be understood that other techniques for isolating adjacent devices may be utilized. In some cases, it may not be necessary to isolate adjacent devices and, thus, amorphized regions (or other features that isolate adjacent devices) may not be present.

Figure 2A:
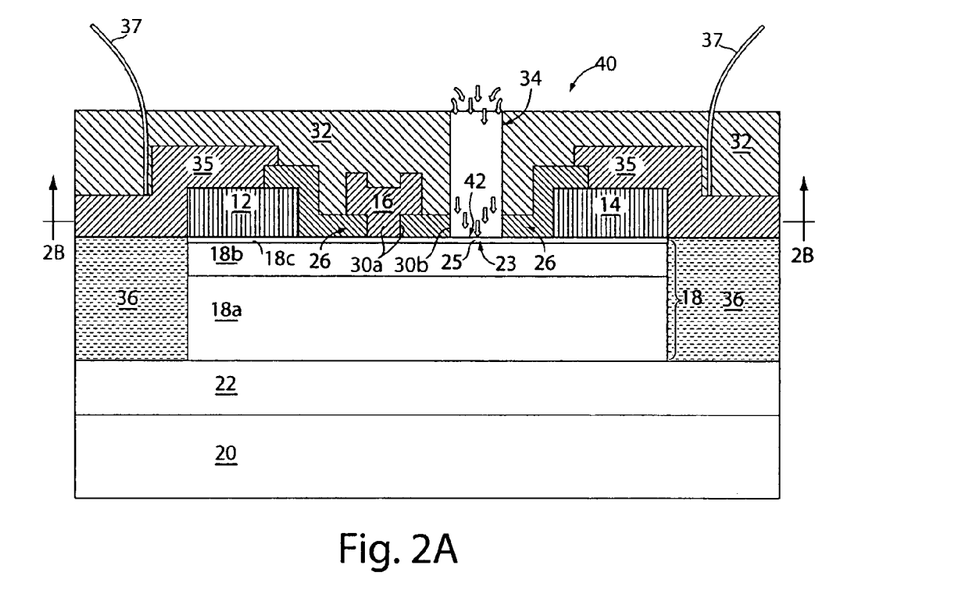
FIG. 2A is a cross-section of a FET-based chemical sensor including an exposed sensing region according to an embodiment of the invention.
Figure 2B:
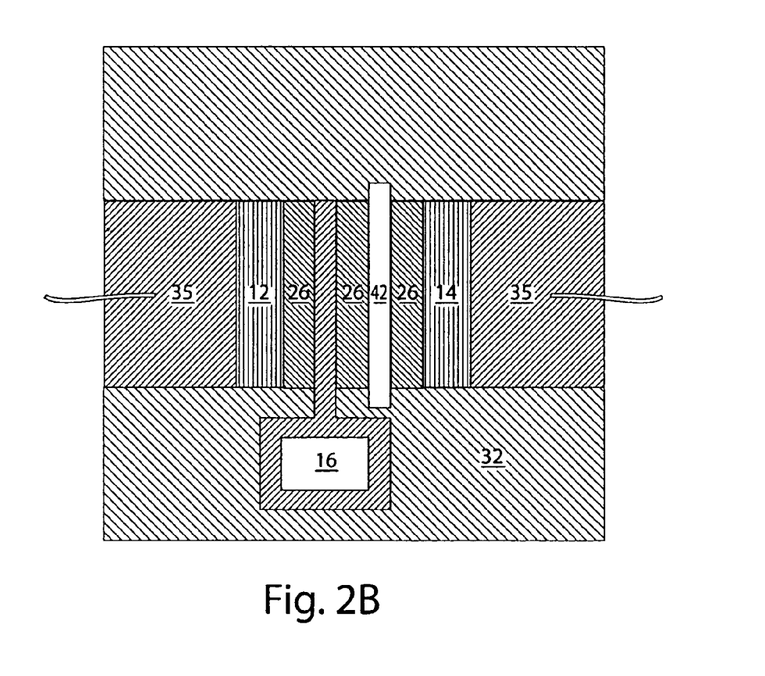
FIG. 2B is a top view of the sensor of FIG. 2A taken along line 2B-2B in FIG. 2A.

FIGS. 2A and 2B illustrate a semiconductor device-based sensor 40 according to another embodiment of the invention. Sensor 40 includes a sensing region 42 which is formed of an exposed surface of semiconductor material (e.g., gallium nitride material) region 18. During operation, in this embodiment, the chemical species are adsorbed directly on sensing region 42. It is believed that, in these embodiments, the surface potential of the semiconductor material (e.g., gallium nitride material) is changed by the adsorption of the chemical species. This change in surface potential leads to a change in a measurable property (e.g., drain current) of the device. As described above, by measuring changes in this property, it is possible to determine the concentration of the species adsorbed and, accordingly, the concentration of the species in the medium in which the sensor is placed.

One advantage associated with the embodiments of FIGS. 2A and 2B is that direct modification of the surface energy of the semiconductor material surface, particularly when the semiconductor material is a gallium nitride material, can lead to increased sensitivity, responsivity and recovery of the sensor. These improved properties arise because the surface potential of the semiconductor material (particularly, when the semiconductor material is a gallium nitride material) can be strongly dependent on the concentration of adsorbed chemical species and also the drain current can be strongly dependent on the surface potential of the semiconductor material region. Thus, adsorption of even a small concentration of chemical species can change the surface potential of the semiconductor region which causes measurable changes in drain current. In some of these embodiments, these sensor properties may be improved relative to certain sensors that do not involve direct adsorption of the chemical species by a semiconductor material region but may involve adsorption by another feature of the structure (e.g., an electrode).

In the embodiments of FIGS. 2A and 2B, the composition of semiconductor material region 18 is selected so that its surface potential is appropriately sensitive to the adsorbed chemical species. Suitable compositions have been described above in connection with FIGS. 1A and 1B including suitable compositions of layers 18b and 18a.

Suitable surface areas for region 42 and ratios of surface area to total device surface area have been described above in connection with FIGS. 1A and 1B.

Figure 3:
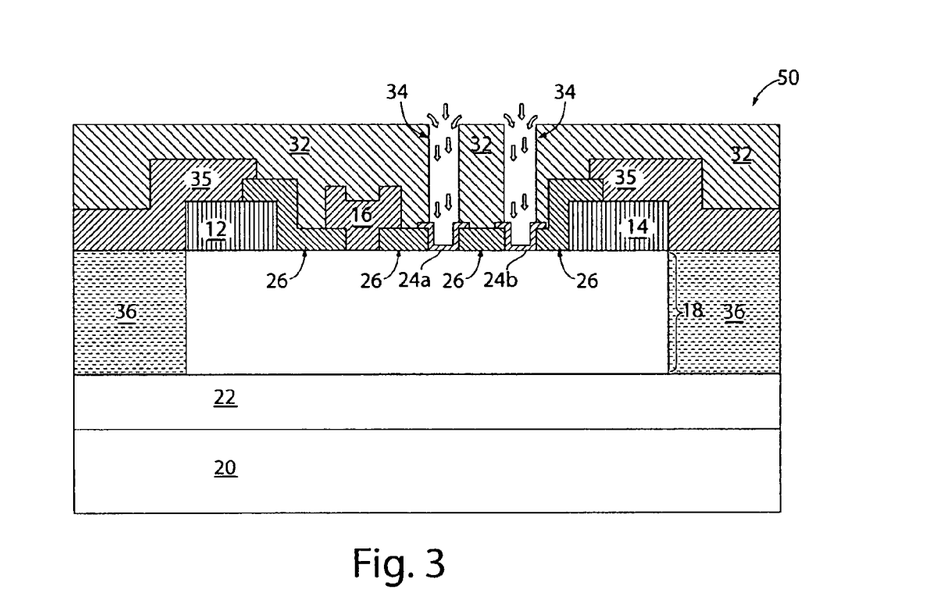
FIG. 3 is a cross-section of a FET-based chemical sensor including two sensing electrodes according to an embodiment of the invention.

FIG. 3 illustrates a semiconductor device-based sensor 50 according to another embodiment of the invention. In this illustrative embodiment, sensor 50 includes a first sensing layer 24a and a second sensing layer 24b, both formed between the source electrode and the drain electrode. One, both, or neither of sensing layers 24a, 24b may be sensing electrodes. The first and second sensing layers may be used to detect the same or different chemical species. In some embodiments, the first and the second sensing layers need not be placed on the same side of the structure, as described further below.

Figure 4:
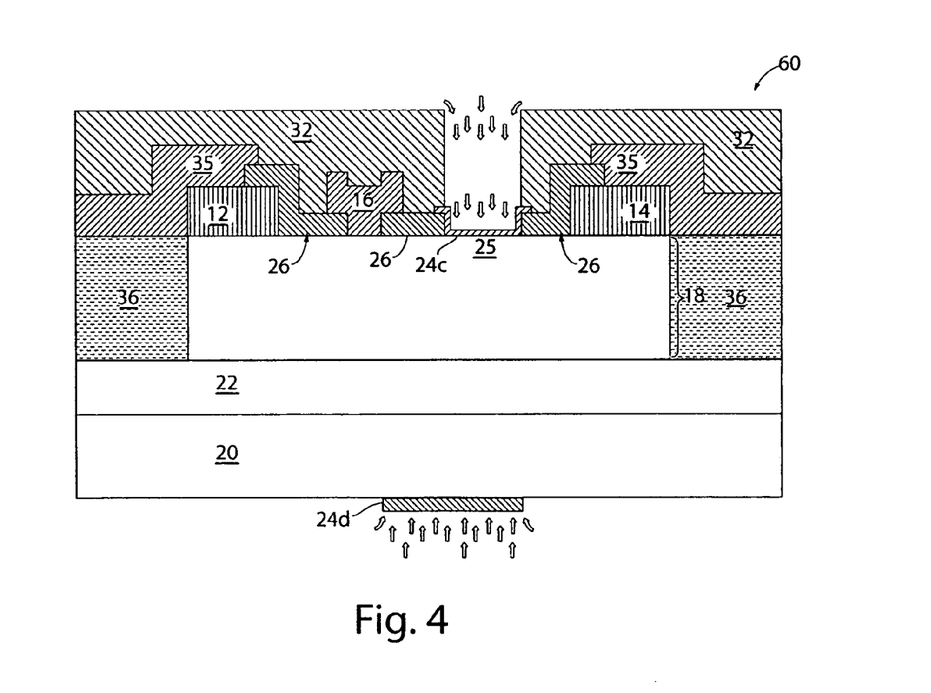
FIG. 4 is a cross-section of a FET-based chemical sensor including two sensing electrodes respectively located on opposite sides of the sensor according to an embodiment of the invention.

FIG. 4 illustrates a semiconductor device-based sensor 60 according to another embodiment of the invention. Sensor 60 includes a first sensing layer 24c formed on a frontside of the sensor and second sensing layer 24d formed on a backside of the sensor. In this illustrative embodiment, the second sensing layer may be associated with a second device (not shown) (e.g., a second FET) formed in, or in regions below the substrate which is separate from the illustrated device formed over the substrate. Providing a sensor that includes two devices may facilitate detection of two species by having the first device detect a first species and the second device detect the second species.

Figure 5:
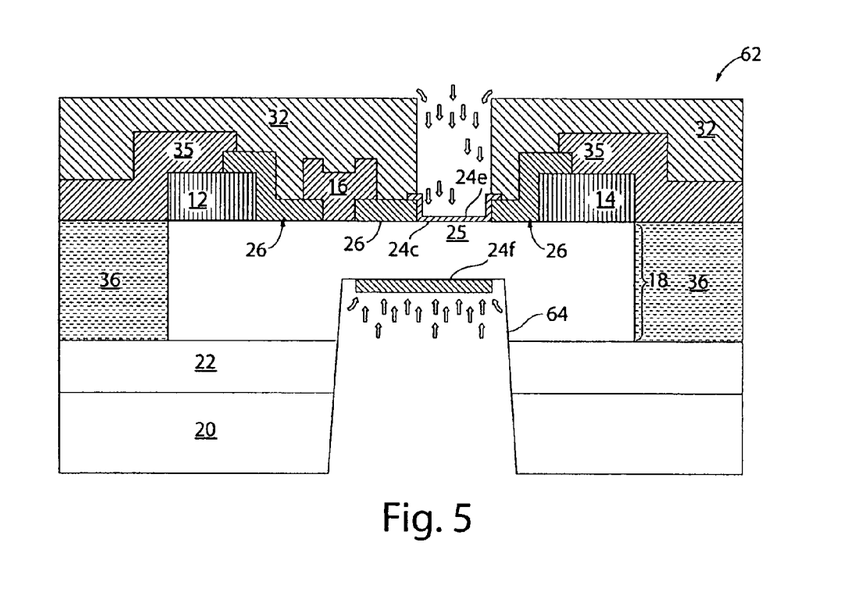
FIG. 5 is a cross-section of a FET-based chemical sensor including two sensing electrodes respectively located on opposite sides of the sensor according to an embodiment of the invention.

FIG. 5 illustrates a semiconductor device-based sensor 62 according to another embodiment of the invention. Sensor 62 includes a first sensing layer 24e formed on a frontside of the sensor and second sensing layer 24f formed in a via 64 that extends from a backside of the sensor. In this illustrative embodiment, the second sensing layer may be associated with the FET device formed over the substrate. That is, the second sensing layer may interact with chemical species which leads to a change in the surface potential of semiconductor material region 18, as described above. Via 64 may also enhance heat removal from the sensor which may be important during operation of the device. Suitable backside vias have been described in commonly-owned U.S. Pat. No. 6,611,002, and in commonly-owned, co-pending U.S. patent application Ser. No. 09/792,409, entitled "Gallium Nitride Materials Including Thermally Conductive Regions", filed Feb. 23, 2001, by Borges et. al., both of which are incorporated herein by reference.

Figure 6:
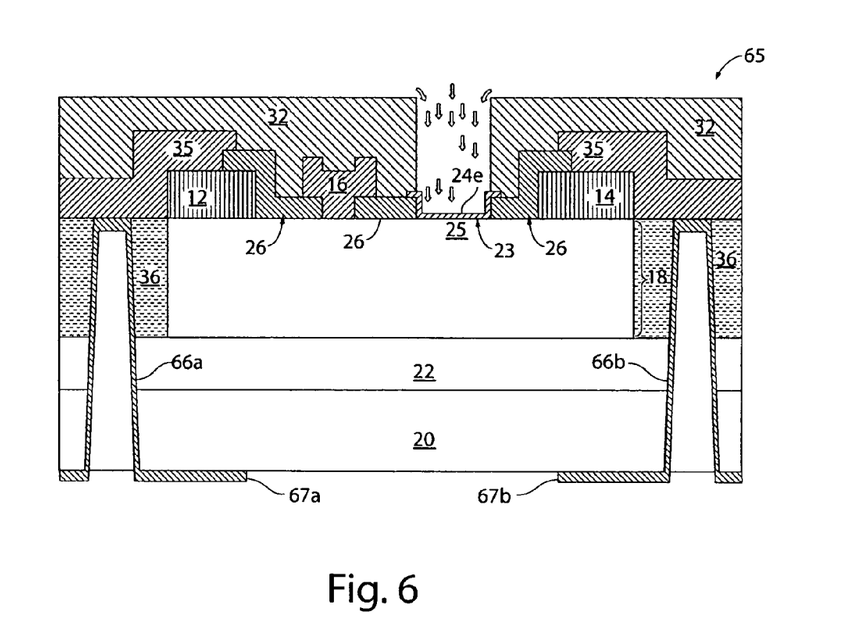
FIG. 6 is a cross-section of a FET-based chemical sensor having backside electrical contacts according to an embodiment of the invention.

FIG. 6 illustrates a semiconductor device-based sensor 65 according to another embodiment of the invention. In this embodiment, vias 66a, 66b (and others not shown) extend from a backside of the sensor. Electrically conductive contacts 67a, 67b (and others not shown) are deposited in respective vias 66a, 66b which are respectively connected to the source electrode 12 and drain electrode 14. Contacts 67a, 67b extend onto the backside of the device. It should be understood that other vias and electrically conductive contacts (both not shown) may be similarly formed for connection to gate electrode 16 and sensing layer 24 (when functioning as a sensing electrode). Bond wires 37 are also provided for connecting the backside contacts to respective voltage sources.

Suitable backside vias have been described in commonly-owned U.S. Pat. No. 6,611,002 and U.S. patent application Ser. No. 09/792,409, both of which are incorporated herein by reference above.

By providing electrically connection to the backside of the device, it is possible to eliminate contacts and bond wires from the frontside of the device. Thus, in these embodiments, the frontside of the device may be free of contacts and bond wires. This enables all areas on the frontside of the device, except for the sensing region, to be encapsulated by encapsulation layer 32. Thus, the encapsulation layer may provide chemical protection for the entire frontside of the device (except for the sensing region). This can be advantageous in applications in which the topside of the device is exposed to a corrosive environment that would otherwise damage electrical contacts, bond wires or others non-encapsulated regions (e.g., proximate electrical contacts) when located on the frontside of the device. Positioning electrical contacts at the backside may also facilitate device packaging.

Figure 7A:
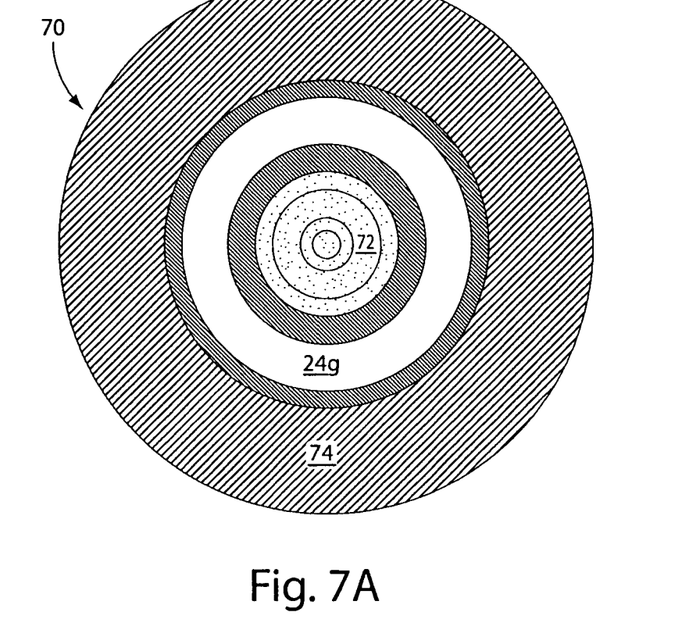
FIGS. 7A and 7B respectively are a top view and a cross-section of a Schottky diode-based chemical sensor according to an embodiment of the invention.
Figure 7B:
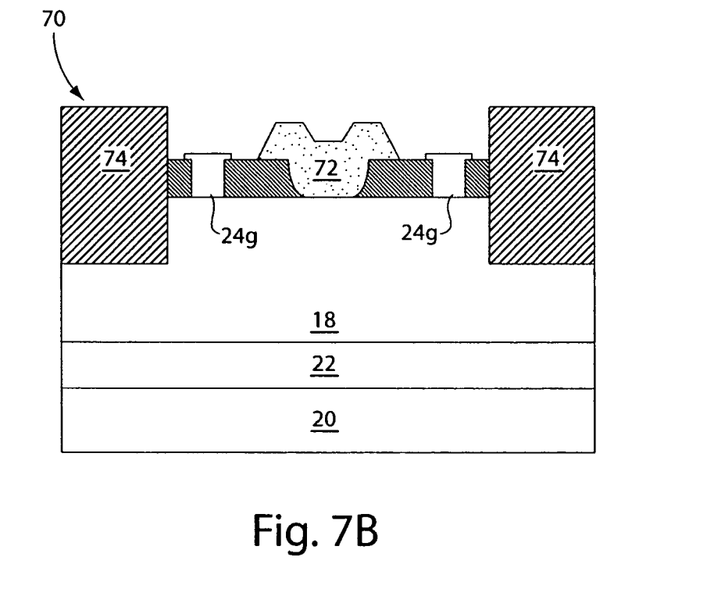

FIGS. 7A and 7B illustrate a semiconductor device-based sensor 70 according to another embodiment of the invention. In this embodiment, sensor 70 is a Schottky diode that include a Schottky electrode 72 and an ohmic electrode 74 that is formed around the diameter of the structure. The sensor further includes a sensing layer 24g (which may be an electrode) between the Schottky electrode and the ohmic electrode which adsorbs chemical species as described above in connection with the other embodiments. As described above, the adsorption of the chemical species results in a change of a measurable property of the sensor (e.g., current).

It should also be understood that, in the embodiments of FIGS. 3-7, the sensing layer(s) may be replaced with a sensing region similar to those illustrated and described above in connection with FIGS. 2A and 2B.

It should be understood that sensors of the invention may be based on other types of semiconductor devices than those illustrated in FIGS. 1-5. For example, other semiconductor devices that have measurable properties that may change in response to adsorption of a chemical species may be utilized.

In general, sensors of the invention may be based on devices that include a sensing electrode, separate from electrodes needed for conventional operation of the device. As described above in connection with the FET embodiment of FIGS. 1A and 1B, the sensing layer may be a sensing electrode separate from the source, drain and gate electrodes. As described above in connection with the Schottky diode embodiment of FIGS. 7A and 7B, the sensing layer may be a sensing electrode separate from the Schottky electrode and the ohmic electrode.

It should also be understood that the chemical sensor may be integrated with other types of devices (e.g., a pressure sensor) in certain embodiments of the invention.

Sensors of the present invention may be used in a wide variety of applications including engine emission monitoring, carbon dioxide detection and flue gas monitoring, amongst others. Also, the sensors of the present invention may be used to detect a wide variety of chemical species including, but not limited to, carbon dioxide, carbon monoxide, hydrogen, oxygen, nitrogen, nitrous oxide, hydrocarbons, alcohols and ionic species, amongst others. In some embodiments of the invention, it may be preferred for the sensors to detect the concentration of gaseous species.

As noted above, during use, the chemical species being detected interact with a sensing region to create a change in the surface potential of an underlying semiconductor material region with this change in surface potential resulting in a change in a property (e.g., drain current) of the device. By measuring the change in the property over time, it is possible to determine the concentration of the species in the medium in which the sensor is placed.

Sensors of the present invention may be formed using methods that employ conventional processing techniques. For example, the layers of the structure may be deposited, patterned and etched using conventional techniques.

Transition layer 22 and semiconductor material (e.g., gallium nitride material) region 18 may be deposited, for example, using metal organic chemical vapor deposition (MOCVD), molecular beam epitaxy (MBE), and hydride vapor phase epitaxy (HVPE), amongst other techniques. The preferred technique may depend, in part, on the composition of the layers. In some cases in which the semiconductor material region comprises gallium nitride material, an MOCVD process may be preferred. A suitable MOCVD process to form a transition layer (e.g., a compositionally-graded transition layer) and gallium nitride material region over a silicon substrate has been described in U.S. Pat. No. 6,649,287 incorporated by reference above. When the semiconductor material region has different layers, in some cases it is preferable to use a single deposition step (e.g., an MOCVD step) to form the entire region 18. When using the single deposition step, the processing parameters are suitably changed at the appropriate time to form the different layers. In certain preferred cases, a single growth step may be used to form the transition layer and the semiconductor material (e.g., gallium nitride material) region.

In other embodiments of the invention (not shown), it is possible to grow a semiconductor material (e.g., gallium nitride material) region using a lateral epitaxial overgrowth (LEO) technique that involves growing an underlying semiconductor material layer through mask openings and then laterally over the mask to form the region, for example, as described in U.S. Pat. No. 6,051,849, which is incorporated herein by reference.

In other embodiments of the invention (not shown), it is possible to grow the semiconductor material (e.g., gallium nitride material) region using a pendeoepitaxial technique that involves growing sidewalls of posts into trenches until growth from adjacent sidewalls coalesces to form a semiconductor material region, for example, as described in U.S. Pat. No. 6,265,289, which is incorporated herein by reference. In these lateral growth techniques, semiconductor material (e.g., gallium nitride material) regions with very low defect densities are achievable. For example, at least a portion of the semiconductor material (e.g., gallium nitride material) region may have a defect density of less than about $10^5$ defects/cm$^2$.

Electrode-defining layer 26 may be deposited using any suitable technique. The technique used, in part, depends on the composition of the electrode-defining layer. Suitable techniques include, but are not limited to CVD, PECVD, LP-CVD, ECR-CVD, ICP-CVD, evaporation and sputtering. When the electrode-defining layer is formed of a silicon nitride material, it may be preferable to use PECVD to deposit the layer.

Source, drain, gate and sensing electrodes may be deposited on the semiconductor material region using known techniques such as an evaporation technique. In cases when the electrodes include two metals, then the metals are typically deposited in successive steps. The deposited metal layer may be patterned using conventional methods to form the electrodes.

When the sensing layer is not an electrode, the sensing layer may be deposited using known techniques which may depend on the composition of the sensing layer.

Suitable techniques for forming electrode-defining layer 26 and electrodes have been described in commonly owned, co-pending U.S. patent application Ser. No. 10/740,376, filed on Dec. 17, 2003, and entitled "Gallium Nitride Material Devices Including an Electrode-Defining Layer and Methods of Forming the Same", which is incorporated herein by reference above.

It should be understood that the invention encompasses other methods than those specifically described herein. Also, variations to the method described above would be known to those of ordinary skill in the art and are within the scope of the invention.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A FET-based chemical sensor designed to detect a chemical species comprising:
   a semiconductor material region comprising a gallium nitride material layer;
   a source electrode formed on the semiconductor material region;
   a drain electrode formed on the semiconductor material region;
   a gate electrode formed on the semiconductor material region; and
   a sensing region comprising the gallium nitride material layer and a sensing electrode, laterally separated from the gate electrode, and capable of interacting with the chemical species to change a measurable property of the chemical sensor.

2. The sensor of claim 1, wherein the sensing region comprises a surface region of the gallium nitride material layer positioned under the sensing electrode.

3. The sensor of claim 1, wherein the sensing region is formed between the source electrode and the drain electrode.

4. The sensor of claim 1, wherein a ratio of sensing electrode surface area to total channel surface area is greater than 0.35.

5. The sensor of claim 1, wherein a separate voltage may be applied to each of the source, drain, gate and sensing electrodes.

6. The sensor of claim 1, further comprising a substrate.

7. The sensor of claim 6, wherein the substrate is a silicon substrate.

8. The sensor of claim 6, further comprising a compositionally-graded transition layer formed between the substrate and the semiconductor material region.

9. The sensor of claim 1, wherein the chemical species is a gaseous species.

10. The sensor of claim 1, wherein the interaction between the chemical species and the sensing region results in a change in the drain current of the sensor.

11. The sensor of claim 1, wherein the interaction between the chemical species and the sensing region changes the surface potential of the gallium nitride material layer.

12. The sensor of claim 1, wherein the chemical species is adsorbed by the sensing region during operation.

13. The sensor of claim 1, wherein the sensing region is positioned between the gate electrode and the drain electrode.

14. The sensor of claim 1, wherein the source, gate and drain electrodes are formed on the gallium nitride material layer.

15. The sensor of claim 1, wherein the gate electrode is isolated from the chemical species.

* * * * *